United States Patent [19]

Shin

[11] 4,209,643

[45] Jun. 24, 1980

[54] PREPARATION OF ACETALS

[75] Inventor: Kju H. Shin, Bloomfield Hills, Mich.

[73] Assignee: Ethyl Corporation, Richmond, Va.

[21] Appl. No.: 967,971

[22] Filed: Dec. 11, 1978

[51] Int. Cl.$^2$ ............................................. C07C 43/30
[52] U.S. Cl. ..................................... 568/594; 260/413; 568/591; 568/592; 568/600
[58] Field of Search ............... 568/594, 591, 592, 600; 562/587; 260/413 Q

[56] References Cited

U.S. PATENT DOCUMENTS

| | | | |
|---|---|---|---|
| 2,491,915 | 12/1949 | Barrick et al. | 568/594 |
| 2,842,576 | 7/1958 | Habeshaw et al. | 568/594 |
| 3,992,432 | 11/1976 | Napier et al. | 260/604 HF |

FOREIGN PATENT DOCUMENTS

| | | | |
|---|---|---|---|
| 715744 | 9/1954 | United Kingdom | 568/594 |
| 721361 | 1/1955 | United Kingdom | 568/594 |

OTHER PUBLICATIONS

Eastman Organic Chemical Bulletin, vol. 48, No. 1, 1976, pp. 1-3.
Jones, Aldrichemica Acta, vol. 9, No. 3, 1976, pp. 35-36.
McCutcheon, Synthetic Detergents, MacNair-Dorland Co., New York, 1950, p. 273.
Condensed Chemical Dictionary, Fifth Ed., Reinhold Publishing Corp., New York, 1956, p. 926.

*Primary Examiner*—Howard T. Mars
*Attorney, Agent, or Firm*—Donald L. Johnson; Robert A. Linn; Willard G. Montgomery

[57] ABSTRACT

A process is described for the production of predominately linear and alpha-branched acetals by reacting a $C_3$ or higher alpha or internal olefin, carbon monoxide, hydrogen, and a $C_1$-$C_5$ alkanol using a cobalt catalyst in the presence of a promoter which is a quaternary ammonium salt such as N-benzyl,N,N,N-trimethylammonium methoxide. When a quaternary ammonium salt is used, an increase in the rate of reaction is effected.

13 Claims, No Drawings

PREPARATION OF ACETALS

BACKGROUND OF THE INVENTION

This invention is directed to a process for preparing acetals from olefins, carbon monoxide, hydrogen and an alkanol using a cobalt catalyst promoted with a quaternary ammonium salt, preferably N-benzyl,N,N,N-trimethylammonium methoxide. It is well known that acetals may be produced from an olefinically unsaturated compound, carbon monoxide and hydrogen in the presence of an alcohol and a catalyst, under suitable conditions of temperature and pressure. U.S. Pat. No. 2,491,915 discloses a process for the preparation of acetals by reacting a mixture of carbon monoxide and hydrogen in the presence of a hydrogenation catalyst with a mixture comprising an olefinic unsaturated compound and a saturated alcohol. British Pat. No. 715,744 discloses a process for the production of a mono-acetal from a mono-olefinically unsaturated compound, other than an aldehyde or acetal of an aldehyde, by reacting the compound with carbon monoxide and hydrogen in the presence of a cobalt catalyst and at elevated temperature and superatmospheric pressure whereby an aldehyde group is introduced at the double bond, thereafter, and without isolation of the aldehydic compound, reacting the product or a part thereof containing said aldehydic compound with a mono- or di-hydric alcohol to convert the aldehydic compound to its acetal and thereafter subjecting the reacted product or part thereof to fractional distillation for the recovery of the acetal. British Pat. No. 721,361 and its counterpart, U.S. Pat. No. 2,842,576, disclose a process for the production of acetals by the Oxo reaction whereby improved yields of acetals are obtained by subjecting an olefinically unsaturated compound, having in the molecule, a functional group other than a free aldehydic group, together with carbon monoxide and hydrogen to the Oxo synthesis reaction in the presence of a mono-hydric or di-hydric alcohol and a cobalt catalyst at elevated temperature and superatmospheric pressure, whereby, in said molecule an aldehydic group is introduced at the double bond, thereafter reacting at least part of the product containing an aldehydic conpound together with the acetal thereof, with a mono- or di-hydric alcohol to convert the aldehydic compound to an acetal and thereafter subjecting the reacted product or part thereof to fractional distillation for recovery of the acetal or acetals.

It has now been discovered that the presence of a quaternary ammonium salt in the reaction of an olefin with carbon monoxide and hydrogen in the presence of an alkanol and a cobalt catalyst has a rate enhancing effect upon the reaction.

SUMMARY OF THE INVENTION

A process for preparing predominately linear and alpha-branched acetals by reacting olefins having about three or more carbon atoms with carbon monoxide, hydrogen, and a $C_1$–$C_5$ alkanol at an elevated temperature and an elevated pressure in the presence of a cobalt catalyst and a quaternary ammonium salt promoter.

DESCRIPTION OF THE PREFERRED EMBODIMENT

A preferred embodiment of the present invention is a process for preparing predominately linear and alpha-branched acetals by reacting olefins having three or more carbon atoms with carbon monoxide, hydrogen, and $C_1$–$C_5$ alkanol at an elevated temperature and at an elevated pressure in the presence of a cobalt catalyst and a quaternary ammonium salt promoter.

A more preferred embodiment of the present invention is a process for preparing predominately linear and alpha-branched acetals by reacting olefins having three or more carbon atoms with carbon monoxide, hydrogen, and a $C_1$–$C_5$ alkanol in the presence of a cobalt catalyst and a quaternary ammonium salt promoter such that the molar ratio of promoter: cobalt is from 1:2 to 1:20 at a temperature of from about 70° C. to about 180° C. and at pressures of from about 400 p.s.i.g. to about 4,000 p.s.i.g. N-benzyl,N,N,N-trimethylammonium methoxide is a most preferred quaternary ammonium salt promoter.

A wide range of olefins can be employed successfully in accordance with this invention. Olefins which are useful in the present process are unsaturated organic compounds having at least one non-aromatic carbon-to-carbon double bond. The double bond may be a terminal double bond or an internal double bond. More preferred olefins are further characterized by having three or more carbon atoms. Cyclic compounds as well as acyclic olefins, branched as well as linear olefins are included. Useful olefins may also contain functional groups such as halide, carboxy, nitro and the like, provided that these functional groups do not enter into or adversely effect the production of acetals in the process of the present invention. Examples of suitable unsaturated compounds which are utilized as the starting material in the process of the present invention include propylene, butene-1, butene-2, isobutene, pentene-1, pentene-2, 2-methylbutene-1, 2-methylbutene-2, hexene-1, 3-methylpentene-1, 2-methylpentene-2, heptene-2, 2-methylhexene-2, 3-methylhexene-2, oxtene-1, octene-2, 3-methylheptene-1, 2-methylheptene-2, nonene-3, 3-methyloctene-2, decene-2, decene-5, 3,4-dimethyloctene-2, 4-ethyloctene-2, undecene-3, undecene-4, 4-methyldecene-2, 4,5-dimethylnonene-2 dodecene-3, tridecene-2, tetradecene-3, pentadecene-5, heptene-1, nonene-1, decene-1, decene-2, decene-3, decene-4, decene-5, undecene-1, dodecene-2, undecene-2, undecene-3, undecene-4, undecene-5, dodecene-1, dodecene-3, dodecene-5, tridecene-1, tridecene-3, tridecene-4, tridecene-6, tetradecene-1, tetradecene-7, pentadecene-1, pentadecene-4, pentadecene6, 2-methoxybutene-2, 2-methoxypentene-1, 2-ethoxyhexene-1, 1-propoxyheptane, 2-ethoxyoctene-1, 2,3-diethoxyundecene-3, 1-chlorobutene-2, 2-chloropentene-1, 2-bromohexene-2, 2,3-dichlorooctene-1, 3-iodooctene-2, 2-methoxy-3-chlorodecene-2, 3,4-dimethyl-2-chlorooctene-2, cyclopentene, cyclohexene, cycloheptene, cyclooctene, cyclononene, cyclodecene, 1-methylcyclohexene-1, 1-ethylcyclohexene-1, 2,3-dipropylcycloheptene-1, 1-methoxycyclopentene-1, 2,3-dipropylcycloheptene-1, 1-chlorocycloheptene-1, 2,3,4-trichlorocyclooctene-1, or mixtures of linear internal olefins such as internal olefins possessing carbon numbers of 8 through 10, 11 through 14 or 15 through 18, etc. Other useful olefins are 4-nitrotridecene-1, oleic acid, 2-chlorododecene-1, 6-phenylundecene-1, ricinoleic acid, 3-hydroxyheptadecene, and the like. Mixtures of alpha and internal olefins are also useful. Further, commercial mixtures of olefins can also be used in the present process.

Commercial mixtures of olefins can also be used in the present process. These commercial olefin mixtures are generally a mixture of various homologous olefins such as $C_4$, $C_6$, $C_8$ olefins; $C_8$, $C_{10}$, $C_{12}$, $C_{14}$, $C_{16}$ olefins; $C_4$, $C_5$, $C_6$, $C_7$ olefins; $C_5$, $C_7$, $C_9$ olefins; $C_{12}$, $C_{14}$ olefins; $C_{12}$, $C_{15}$, $C_{17}$ olefins; $C_{12}$, $C_{13}$, $C_{14}$, $C_{15}$, $C_{16}$ olefins; $C_{22}$, $C_{24}$, $C_{26}$, olefins; $C_{30}$, $C_{32}$, $C_{34}$, $C_{36}$ olefins; $C_{40}$ and higher olefin mixtures and the like. These commercial mixtures are synthesized for example by Ziegler catalyst polymerization of low molecular weight olefins such as ethylene or propylene; by dehydrogenation of suitable paraffins and the like. These commercial olefin mixtures can contain branched as well as straight-chain olefins; α-olefins as well as internal olefins. The mixed olefins thus obtained might also contain minor amounts of non-homologous olefins as well as non-olefin components. Such non-olefin components might be paraffins, alkyl halides, alcohols and the like; the nature of the non-olefin components is to a great degree dependent on the synthesis route utilized. Commercial mixtures containing even carbon numbered olefins ranging from $C_4$-$C_{14}$ are useful; such mixtures containing $C_4$-$C_6$ olefins; $C_4$, $C_6$ and $C_8$ olefins; $C_4$-$C_8$ olefins; $C_8$-$C_{10}$ olefins; $C_{10}$, $C_{12}$ and $C_{14}$ olefins are particularly useful. The mixed olefins obtained from such a commercial synthesis can be used as such in the present process and need not be separated into the individual components to be useful.

It is understood that the aforementioned unsaturated compounds are only representative classes of compounds which may be employed as the starting material of the process of the present invention and that the present invention is not necessarily limited thereto.

The alkanols used as a reactant in the present process are normally liquid lower molecular weight alkanol. They include primary and secondary alkanols. Useful alkanols are 2-docecanol, isopropanol, cyclohexanol, 2,2-dimethylpropanol and the like. Monohydroxy alkanols having from 1 to 5 carbon atoms are preferred. Examples of preferred alkanols are ethanol, n-pentanol, 2-methylpropanol, n-butanol and the like. Methanol is a most preferred alkanol.

Sufficient alkanol is ordinarily used to provide at least two moles of alkanol per mole of olefin. An excess of alkanol however can be used, thus, alkanol:olefin molar ratios of 2:1 to 10:1 are useful. Preferred molar ratios of alkanol:olefin are 2.2:1 to about 4:1.

A cobalt catalyst is utilized in the present process. Any cobalt-containing compound capable of forming a cobalt carbonyl under the reaction conditions can be used. Dicobalt octacarbonyl is the most preferred cobalt compound. The cobalt catalyst concentration may be varied. Generally, amounts of catalyst sufficient to provide from 1 to 1,000 moles of cobalt per molecule of olefin are used. A preferred cobalt; olefin mole ratio is about 1:100.

The present reaction is carried out at temperatures from about 70° C. to about 180° C. A preferred temperature range is from about 90° C. to about 110° C.; a most preferred reaction temperature is 110° C.

The process is ordinarily carried out under pressure. This pressure is primarily due to the carbon monoxide (CO) and hydrogen reactants. Thus, pressure ranges from about 400 p.s.i.g. to about 4,000 p.s.i.g. can be used. Reaction pressures from about 800 p.s.i.g. to about 1,200 p.s.i.g. are preferred. The mole ratio of hydrogen to carbon monoxide is from about 4:1 to about 1:4 and preferably from about 1:1 to about 1:3.

The reaction time may be varied. It is dependent to some degree on the other parameters such as pressure, temperature, nature of the reactants and the like. Generally, the reaction is carried out for from 15 minutes up to about 10 hours or more.

The product obtained in the present process comprises a mixture consisting predominately of linear and branched acetals with some aldehyde. This can be illustrated by the following reaction equation:

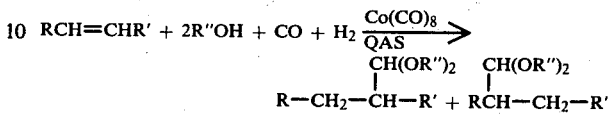

wherein R and R' are hydrogen or $C_1$ and higher; and R" is $C_1$-$C_5$.

A primary feature of the present invention is the addition of small amounts of a quaternary ammonium salt as a promoter in the process ilustrated by the equation above. It has been found that the presence of such a promoter has a rate enhancing effect upon the reaction. By rate enhancing effect is meant that the rate of the reaction is increased over that of a system without the quaternary ammonium salt compound. The improvement in rate is generally indicated by an increase in the amount of acetal formed compared with the other reaction products for a given period of time over that of a system without the quaternary ammonium salt promoter for the same period of time.

The quaternary ammonium salts which may be used as promoters in the present process are characterized as having the following formula:

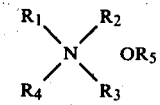

wherein $R_1$, $R_2$, $R_3$ and $R_4$ are alkyl, aralkyl, cycloalkyl or aryl in which the total number of carbon atoms is from 4 to 60 carbon atoms; and $R_5$ is H, $CH_3$, $C_2H_5$

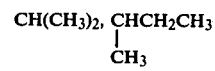

Quaternary ammonium salts which may be used as promoters in the present process include but are not limited to the following:
Benzyltrimethylammonium Methoxide
Benzyltriethylammonium Ethoxide
Benzyltriethylammonium Propoxide
Benzyltriethylammonium Hydroxide
Benzyltrimethylammonium Methoxide
Benzyltrimethylammonium Ethoxide
Benzyltrimethylammonium Propoxide
Benzyltrimethylammonium Hydroxide
Benzyltriphenylphosphonium Methoxide
Benzyltriphenylphosphonium Ethoxide
Benzyltriphenylphosphonium Propoxide
Benzyltriphenylphosphonium Hydroxide
Didodecyldimethylammonium Methoxide
Didodecyldimethylammonium Ethoxide
Didodecyldimethylammonium Propoxide
Didodecyldimethylammonium Hydroxide
Hexadecyltrimethylammonium Methoxide Hexadecyltrimethylammonium Ethoxide
Hexadecyltrimethylammonium Propoxide
Hexadecyltrimethylammonium Hydroxide
Tetrabutylammonium Methoxide
Tetrabutylammonium Ethoxide
Tetrabutylammonium Propoxide
Tetrabutylammonium Hydroxide
Benzyldimethylphenylammonium Methoxide
Benzyldimethylphenylammonium Ethoxide
Benzyldimethylphenylammonium Propoxide
Benzyldimethylphenylammonium Hydroxide
Decyltrimethylammonium Methoxide
Decyltrimethylammonium Ethoxide
Decyltrimethylammonium Propoxide
Decyltrimethylammonium Hydroxide
Dimethyldioctadecylammonium Methoxide
Dimethyldioctadecylammonium Ethoxide
Dimethyldioctadecylammonium Propoxide
Dimethyldioctadecylammonium Hydroxide
Dodecyltrimethylammonium Methoxide
Dodecyltrimethylammonium Ethoxide
Dodecyltrimethylammonium Propoxide
Dodecyltrimethylammonium Hydroxide
Ethylhexadecyldimethylammonium Methoxide
Ethylhexadecyldimethylammonium Ethoxide
Ethylhexadecyldimethylammonium Propoxide
Ethylhexadecyldimethylammonium Hydroxide
Nonyltrimethylammonium Methoxide
Nonyltrimethylammonium Ethoxide
Nonyltrimethylammonium Propoxide
Nonyltrimethylammonium Hydroxide
Tetraethylammonium Methoxide
Tetraethylammonium Ethoxide
Tetraethylammonium Propoxide
Tetraethylammonium Hydroxide
Tetrahexylammonium Methoxide
Tetrahexylammonium Ethoxide
Tetrahexylammonium Propoxide
Tetrahexylammonium Hydroxide
Tetraheptylammonium Methoxide
Tetraheptylammonium Ethoxide
Tetraheptylammonium Propoxide
Tetraheptylammonium Hydroxide
Tetrapentylammonium Methoxide
Tetrapentylammonium Ethoxide
Tetrapentylammonium Propoxide
Tetrapentylammonium Hydroxide
Tetra-iso-pentylammonium Methoxide
Tetra-iso-pentylammonium Ethoxide
Tetra-iso-pentylammonium Propoxide
Tetra-iso-pentylammonium Hydroxide
Tetrapropylammonium Methoxide
Tetrapropylammonium Ethoxide
Tetrapropylammonium Propoxide
Tetrapropylammonium Hydroxide
Triethylmethylammonium Methoxide
Triethylmethylammonium Ethoxide
Triethylmethylammonium Propoxide
Triethylmethylammonium Hydroxide
Triethylphenylammonium Methoxide
Triethylphenylammonium Ethoxide
Triethylphenylammonium Propoxide
Triethylphenylammonium Hydroxide
Triethylpropylammonium Methoxide
Triethylpropylammonium Ethoxide
Triethylpropylammonium Propoxide
Triethylpropylammonium Hydroxide
Trioctylpropylammonium Methoxide
Trioctylpropylammonium Ethoxide
Trioctylpropylammonium Propoxide
Trioctylpropylammonium Hydroxide
N-benzyl-N,N,N-trimethylammonium Methoxide
N-benzyl-N,N,N-trimethylammonium Ethoxide
N-benzyl-N,N,N-trimethylammonium Propoxide
N-benzyl-N,N,N-trimethylammonium Hydroxide Some of the foregoing quaternary ammonium salts are more preferrable than others because they are more effective and/or available. N-benzyl-N,N,N-trimethylammonium methoxide is a most preferred promoter.

The concentration of the promoter is conveniently based on the amounts of cobalt present in the cobalt catalyst expressed in terms of molar ratio of the promoter:cobalt (in the cobalt catalyst). Useful promoter ratios are 1:2 to 1:20, with a 1:4.3 ratio being most preferable.

The following series of examples will serve to illustrate the present invention.

GENERAL PROCEDURE

The olefin, catalyst, alcohol and promoter (when added) where charged to a suitably sized autoclave. The autoclave was then sealed. A gaseous mixture of carbon monoxide and hydrogen was then charged to the autoclave. The mixture was then heated with stirring under pressure until the desired reaction temperature and pressure was reached. The reaction was continued at this temperature and pressure in the autoclave for the desired length of time. The autoclave was then cooled and vented. The yield of product was then obtained and it was analyzed by Vapor Phase Chromatography. In all of the examples yield figures based on analysis by Vapor Phase Chromatography are in area percent. Olefin conversion is a measure of the amount of olefin reactant which is converted to acetal/aldehyde product. It is ordinarily expressed as percent conversion. The yield, on the other hand, is the percent of converted olefin which is either acetal or aldehyde.

EXAMPLE I

An autoclave was charged with 0.4 moles of dodecene-1, 1.6 moles of methanol and 0.0072 moles of dicobalt octacarbonyl. The autoclave was then sealed and a gaseous mixture of carbon monoxide and hydrogen having a mole ratio of carbon monoxide to hydrogen of 1:1 was charged to the autoclave. The mixture was heated with stirring to 110° C. The pressure at this temperature was approximately 700 p.s.i.g. to about 900 p.s.i.g. The reaction was continued at this temperature and pressure for approximately 2 hours. Analysis of the product by Vapor Phase Chromatography approximately 15 minutes after the start of reaction indicated a 76.1% conversion of olefin and a 68% yield of acetal. Analysis of the product at the end of approximately 2.5 hours after the start of reaction indicated a 97.3% conversion and a 63% yield of acetal. Analysis of the product made at the end of the reaction indicated a 99.4% conversion and an 82% yield of acetal.

EXAMPLE II

The general procedure of Example I was repeated except that 0.4 grams of N-benzyl,N,N,N-trimethylammonium methoxide was added to the reaction mixture in the autoclave. Analysis of the product by Vapor Phase Chromatography made approximately 15 minutes after the start of the reaction indicated an 80.6% conversion and a 70% yield of acetal. Analysis made at the end of approximately 2.5 hours indicated substantially 100% conversion and a 90% yield of acetal.

As can be seen by comparing Examples I and II conversion of alpha-olefin, carbon monoxide, hydrogen, and alkanol using a cobalt containing catalyst is most effective when the reaction is carried out in the presence of a quaternary ammonium salt promoter such as N-benzyl,N,N,N-trimethylammonium methoxide. The increased yields of acetal obtained by carrying out the reaction in the presence of a quaternary ammonium salt promoter are best demonstrated by comparing the yield of acetal obtained at the end of 2.5 hours from the start of the reaction, as disclosed in Example II, in which a promoter was used, with the yield of acetal obtained at the end of 2.5 hours after the start of reaction in Example I in which no promoter was used. There is approximately a 30% greater yield of acetal when the reaction is carried out in the presence of the N-benzyl,N,N,N-trimethylammonium methoxide promoter.

EXAMPLE III

An autoclave was charged with 0.4 moles of a mixture of $C_{12}$ olefin consisting predominately of internal olefin, 1.6 moles methanol and 0.0072 moles of dicobalt octacarbonyl. The autoclave was then sealed and a gaseous mixture of carbon monoxide and hydrogen having a mole ratio of carbon monoxide to hydrogen of 1:1 was charged to the autoclave. The mixture was heated with stirring to 110° C. The pressure at this temperature was approximately 800 p.s.i.g. to about 900 p.s.i.g. The reaction was continued at this temperature and pressure for approximately 5.5 hours. Analysis of the product by Vapor Phase Chromatography approximately 5 minutes after the start of the reaction indicated a 54.1% conversion and a 63% yield of acetal. Analysis at the end of approximately 1.25 hours from the start of reaction indicated an 85.5% conversion and approximately a 57% yield of acetal. Analysis made at the end of the reaction indicated substantially 100% conversion and an 86% yield of acetal.

EXAMPLE IV

The general procedure of Example III was repeated except that 2.0 grams of N-benzyl,N,N,N-trimethylammonium methoxide was added to the reaction mixture in the autoclave. Analysis of the product by Vapor Phase Chromatography made approximately 5 minutes after the start of reaction indicated a 48.7% conversion and a 68% yield of acetal. Analysis made approximately 1.25 hours after the start of the reaction indicated an 82.3% conversion and a 79% yield of acetal. Analysis made at the end of the reaction indicated substantially 100% conversion and approximately 86% yield of acetal.

As can be seen from Examples III and IV, the presence of a quaternary ammonium salt promoter in the reaction also has a rate enhancing effect on the formation of acetals when the olefin reactant is comprised predominately of internal olefin as well as alpha olefin. A comparison of Examples III and IV also shows the yield of acetal at the end of 1.25 hours from the start of reaction is approximately 20% more when a quaternary ammonium salt promoter is present in the reaction.

EXAMPLE V

An autoclave was charged with 0.4 moles of a mixture of random $C_{12}$ olefin, 1.6 moles of methanol, 0.0072 moles of dicobalt octacarbonyl and 0.4 grams of N-benzyl,N,N,N-trimethylammonium methoxide. The autoclave was then sealed and a gaseous mixture of carbon monoxide and hydrogen having a mole ratio of carbon monoxide to hydrogen of 1:1 was charged to the autoclave. The mixture was heated with stirring to 110° C. The pressure at this temperature was approximately 800 p.s.i.g. to 900 p.s.i.g. The reaction was continued at this temperature and pressure for approximately 1.5 hours. Analysis of the reaction mixture of Vapor Phase Chromatography at the end of 1.5 hours indicated an 81.1% conversion and a 78.7% yield of acetal.

EXAMPLE VI

An autoclave was charged with 0.4 moles of a mixture of random $C_{12}$ olefin, 1.6 moles of methanol, 0.0072 moles of dicobalt octacarbonyl and 0.4 grams of N-benzyl,N,N,N-trimethylammonium methoxide. The autoclave was then sealed and a gaseous mixture of carbon monoxide to hydrogen having a mole ratio of carbon monoxide to hydrogen of 1:1 was charged to the autoclave. The mixture was heated with stirring to 110° C. The pressure at this temperature was approximately 400 p.s.i.g. to 520 p.s.i.g. The reaction was continued at this temperature and pressure for approximately 3.5 hours. Analysis of the reaction mixture by Vapor Phase Chromatography at the end of 3.5 hours indicated at 78.4% conversion and a 73% yield of acetal.

EXAMPLE VII

An autoclave was charged with 0.4 moles of a mixture of random $C_{12}$ olefin, 0.9 moles of methanol, 0.0072 moles of dicobalt octacarbonyl and 0.2 grams N-benzyl,N,N,N-trimethylammonium methoxide. The autoclave was then sealed and gaseous mixture of carbon monoxide and hydrogen having a mole ratio of carbon monoxide to hydrogen of 1:1 was charged to the autoclave. The mixture was heated with stirring to 150° C. The pressure at this temperature was approximately 600 p.s.i.g. to 1000 p.s.i.g. The reaction was continued at this temperature and pressure for approximately 1.25 hours. Analysis of the reaction mixture by Vapor Phase Chromatography at the end of 1.25 hours indicated a 97.1% conversion and a 61% yield of acetal. The lower yield of acetal in this particular run was due to the unexplained presence of heavy ends in the reaction product. The yield of heavy ends in this reaction was approximately 18.2%.

EXAMPLE VIII

An autoclave was charged with 0.4 moles of a mixture of random $C_{12}$ olefin, 1.6 moles of methanol, 0.0072 moles of dicobalt octacarbonyl and 0.4 grams N-benzyl,N,N,N-trimethylammonium methoxide. The autoclave was then sealed and a gaseous mixture of carbon monoxide and hydrogen having a mole ratio of carbon monoxide to hydrogen of 2:1 was charged to the autoclave. The mixture was heated with stirring to 90° C. The pressure at this temperature was approximately 750 p.s.i.g. to about 1,000 p.s.i.g. The reaction was continued at this temperature and pressure for approximately 8.6 hours. Analysis of the reaction mixture by Vapor Phase Chromatography at the end of 8.6 hours indicated a conversion of 59.3% and an 88% yield of acetal.

EXAMPLE IX

An autoclave was charged with 0.4 moles of a mixture of random $C_{12}$ olefin, 1.6 moles of methanol, 0.0072 moles of dicobalt octacarbonyl and 0.4 grams of N-benzyl, N,N,N-trimethylammonium methoxide. The autoclave was then sealed and a gaseous mixture of carbon monoxide and hydrogen having a mole ratio of 3:1 was charged to the autoclave. The mixture was then heated with stirring to 90° C. The pressure at this temperature was approximately 800 p.s.i.g. to about 1,000 p.s.i.g. The reaction was continued at this temperature and pressure for approximately 1.8 hours. Analysis of the reaction mixture by Vapor Phase Chromatography at the end of 1.8 hours indicated a 32.4% conversion and 84% yield of acetal.

Reaction pressure has an effect on olefin conversion and acetal yield in the present process. The following example illustrates the effect of lowering the pressure to a range of from 200 p.s.i.g. to about 250 p.s.i.g. (measured at 110° C.).

EXAMPLE X

The general procedure of Example III was repeated except that 0.4 grams of N-benzyl,N,N,N-trimethylammonium methoxide was used in the reaction instead of 2.0 grams and the reaction was carried out at a pressure of from about 200 p.s.i.g. to about 250 p.s.i.g. instead of from about 800 p.s.i.g. to about 1000 p.s.i.g. Analysis of the reaction mixture by Vapor Phase Chromatography at the end of 4.5 hours indicated a 13.4% conversion and a 63% yield of acetal. This, when compared to Example III in which a substantially 100% conversion and an 86% yield of acetal was obtained at the end of 5.5 hours after the start of the reaction at pressures ranging from about 800 p.s.i.g. to about 900 p.s.i.g. indicates that pressures substantially above 250 p.s.i.g. should be used if high conversion and acetal yield are desired.

EXAMPLE XI

An autoclave was charged with 0.4 moles of dodecene-1, 1.6 moles of methanol, 0.0072 moles of dicobalt octacarbonyl and 0.4 grams of N-benzyl,N,N,N-trimethylammonium methoxide. The autoclave was then sealed and a gaseous mixture of carbon monoxide and hydrogen having a mole ratio of carbon monoxide to hydrogen of 1:1 was charged to the autoclave. The mixture was then heated with stirring to 90° C. The pressure at this temperature was approximately 2,500 p.s.i.g. to about 3,000 p.s.i.g. The reaction was continued at this temperature and pressure for approximately 2 hours. Analysis of the reaction mixture by Vapor Phase Chromatography at the end of 0.75 hours indicated a 63.5% conversion and a 93% yield of acetal. Analysis of the reaction mixture at the end of two hours indicated substantially 100% conversion and an 89% yield of acetal.

EXAMPLE XII

An autoclave was charged with 0.4 moles of dodecene-1, 1.6 moles of methanol, 0.0072 moles of dicobalt octacarbonyl and 0.4 grams of N-benzyl,N,N,N-trimethylammonium hydroxide. The autoclave was then sealed and a gaseous mixture of carbon monoxide and hydrogen having a mole ratio of carbon monoxide to hydrogen of 1:1 was charged to the autoclave. The mixture was then heated with stirring to 90° C. The pressure at this temperature was approximately 2,500 p.s.i.g. to about 3,000 p.s.i.g. The reaction was continued at this temperature and pressure for approximately 3 hours. Analysis of the reaction mixture by Vapor Phase Chromatography at the end of 3 hours indicated a 97.6% conversion and an 87% yield fo acetal.

EXAMPLE XIII

An autoclave was charged with 0.4 moles of a mixture of random $C_{12}$ olefin, 1.6 moles of methanol, 0.0072 moles of dicobalt octacarbonyl and 0.4 grams of N-benzyl,N,N,N-triethylammonium methoxide. The autoclave was then sealed and a gaseous mixture of carbon monoxide and hydrogen of 1:1 was charged to the autoclave. The mixture was then heated with stirring to 110° C. The pressure at this temperature was approximately 800 p.s.i.g. to about 900 p.s.i.g. The reaction was continued at this temperature and pressure for approximately 2 hours. Analysis of the reaction mixture by Vapor Phase Chromatography at the end of 1.5 hours indicated a 32.5% conversion and a 74% yield of acetal. Analysis of the reaction mixture at the end of 2 hours indicated an 88.4% conversion and a 78% yield of acetal.

EXAMPLE XIV

An autoclave was charged with 0.4 moles of a mixture of random $C_{12}$ olefin, 1.6 moles of methanol, 0.0072 moles of dicobalt octacarbonyl and 2.0 grams of tetrabutylammonium hydroxide. The autoclave was then sealed and a gaseous mixture of carbon monoxide and hydrogen having a mole ratio of carbon monoxide to hydrogen 1:1 was charged to the autoclave. The mixture was then heated with stirring to 110° C. The pressure at this temperature was approximately 800 p.s.i.g. to about 1,000 p.s.i.g. The reaction was continued at this temperature and pressure for approximately 2.7 hours. Analysis of the reaction mixture by Vapor Phase Chromatography at the end of 2.7 hours indicated a 95% conversion and a 71% yield of acetal.

Claims to the invention follow.

I claim:

1. A process for preparing linear and alpha-branched acetals by reacting olefin having 3 or more carbon atoms with carbon monoxide, hydrogen and a $C_1$–$C_5$ alkanol at a temperature of from about 70° C. to about 180° C. and a pressure of from about 400 psig to about 4000 psig in the presence of a cobalt catalyst and a quaternary ammonium salt promoter characterized as having the following formula:

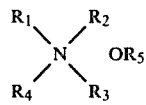

wherein $R_1$, $R_2$, $R_3$ and $R_4$ are alkyl, aralkyl, cycloalkyl or aryl in which the total number of carbon atoms is from 4 to 60 and $R_5$ is H, $CH_3$, $C_2H_5$, $CH(CH_3)_2$ or

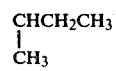

wherein the promoter: cobalt molar ratio is from about 1:2 to about 1:20.

2. The process of claim 1 wherein said olefins are hydrocarbon monoolefin selected from alpha-olefin, internal olefin, and mixtures thereof.

3. The process of claim 1 wherein said alkanol is methanol.

4. The process of claim 1 wherein said catalyst is dicobalt octacarbonyl.

5. The process of claim 1 wherein said promoter is N-benzyl,N,N,N-trimethylammonium methoxide.

6. The process of claim 1 wherein said promoter is N-benzyl,N,N,N-trimethylammonium hydroxide.

7. The process of claim 1 wherein said promoter is N-benzyl,N,N,N-triethylammonium methoxide.

8. The process of claim 1 wherein said promoter is tetrabutylammonium hydroxide.

9. The process of claim 2 wherein said olefin is a mixture of olefins in the range of from about $C_3$–$C_{32}$.

10. The process of claim 9 wherein said olefin mixtures are predominately alpha, even carbon number olefins in the range of from about $C_4$–$C_{18}$.

11. The process of claim 9 wherein said olefin mixtures are predominately random, even carbon number olefins in the range of from about $C_4$–$C_{18}$.

12. The process of claim 2 wherein the promoter cobalt matter ratio is about 1:4.3.

13. The process of claim 2 wherein said olefin is dodecene-1.

* * * * *